(12) United States Patent
Johansson

(10) Patent No.: US 8,790,588 B2
(45) Date of Patent: Jul. 29, 2014

(54) OUTLET DEVICE FOR DISINFECTION APPARATUS AND METHOD FOR LIQUID TRANSFER

(75) Inventor: Jonas Johansson, Växjö (SE)

(73) Assignee: Getinge Disinfection AB, Vaxjo (SE)

( * ) Notice: Subject to any disclaimer, the term of this patent is extended or adjusted under 35 U.S.C. 154(b) by 1141 days.

(21) Appl. No.: 12/308,094

(22) PCT Filed: Jun. 16, 2007

(86) PCT No.: PCT/EP2007/005320
§ 371 (c)(1),
(2), (4) Date: Dec. 8, 2008

(87) PCT Pub. No.: WO2007/147537
PCT Pub. Date: Dec. 27, 2007

(65) Prior Publication Data
US 2009/0165862 A1    Jul. 2, 2009

(30) Foreign Application Priority Data

Jun. 21, 2006 (EP) ..................................... 06115776

(51) Int. Cl.
*A61L 2/18* (2006.01)
(52) U.S. Cl.
CPC ........................................ *A61L 2/18* (2013.01)
USPC ........................................... 422/292; 422/28
(58) Field of Classification Search
USPC ....................................... 422/28, 292; 137/13
See application file for complete search history.

(56) References Cited

U.S. PATENT DOCUMENTS

| 3,034,519 | A | * | 5/1962 | Jacobs | ......................... 134/95.3 |
| 3,092,120 | A | * | 6/1963 | Hilger et al. | ..................... 134/47 |
| 5,183,066 | A | * | 2/1993 | Hethcoat | ......................... 134/54 |
| 5,522,410 | A | * | 6/1996 | Meilleur | ..................... 134/57 R |

FOREIGN PATENT DOCUMENTS

| DE | 41 22 724 | 1/1993 |
| EP | 1 186 308 | 3/2002 |
| FR | 2 790 688 | 9/2000 |
| GB | 600 225 | 4/1948 |
| GB | 2 237 816 | 5/1991 |

* cited by examiner

*Primary Examiner* — Sean E Conley
(74) *Attorney, Agent, or Firm* — Harness, Dickey & Pierce, PLC

(57) ABSTRACT

An embodiment of the present invention discloses a method for liquid transfer and a liquid disinfection apparatus for cleaning of objects, such as health care objects. The disinfection apparatus includes a chamber which is arranged to receive said objects for cleaning, a spray system including nozzles for distributing liquid in the chamber, and an outlet tank connected to a sewer system. The chamber is adapted to receive a liquid volume which is being circulated by the spray system including nozzles for cleaning of objects. In at least one embodiment, the disinfection apparatus further includes a rapid transfer port which is liquid flow connected between the chamber and an outlet tank so as to constitute an immediate transfer of the first volume from the chamber to the outlet tank, essentially without any tubing arranged between the chamber and the outlet tank.

18 Claims, 6 Drawing Sheets

OUTLET DEVICE FOR DISINFECTION APPARATUS AND METHOD FOR LIQUID TRANSFER

FIELD OF THE INVENTION

The present invention relates to a method for liquid transfer of a disinfection apparatus. The invention also relates to a liquid disinfection apparatus for cleaning of objects, such as health care objects, which disinfection apparatus comprises; a chamber which is arranged to receive the objects for cleaning, a spray system comprising nozzles for distributing liquid in the chamber, and an outlet tank connected to a sewer system.

BACKGROUND ART

Disinfection apparatus of the above type are well known and are also called washer disinfector. They are regulated under disinfection standards. Washer disinfectors are used for cleaning and disinfection of goods, instruments and other objects that are used in, for instance, hospitals, laboratories and in the pharmaceutical industry. As examples of such objects, mention can be made of vessels of different kinds, instruments containers, surgery equipments, instruments, machine parts in nursing applications and other related objects.

Generally, the major part of the liquid used in a washer disinfector is normally water. A known way to empty the chamber from water is to use a sump pump arranged in the bottom of the chamber. One part of the liquid used in the chamber is pumped back to a tank for recirculation to the chamber and another part is pumped to a drain tank.

Another known way to empty a chamber of a washer disinfector is that the outlet of the chamber is connected to a tube divided into a circulation tube and a drain tube. The circulation tube is arranged to circulate the liquid back to a disinfectant tank and the drain tube is connected to a drain tank.

However, the flow and other parameters that are being regulated in a washer disinfector may be troublesome to control in an efficient manner. In addition to complexity, the process of the disinfection apparatus may be time-consuming.

It is desirable to reduce the process time of a disinfection apparatus. Also it is suitable to reduce the liquid volume needed in the process. Moreover it is desirable to reduce the costs and the number of machine components of the disinfection apparatus and yet maintain its desired disinfection function.

Also, it is advantageous to provide a robust, cost effective and reliable high quality disinfection apparatus.

SUMMARY OF THE INVENTION

The object of the invention is to provide a disinfection apparatus and a method for liquid transfer in a disinfection apparatus which allows improvements in relation to prior-art disinfection apparatus and methods therefore in one or more of the above aspects.

In one aspect of the present invention, the above objects are achieved by a method for liquid transfer in a disinfection program of a disinfection apparatus, comprising a chamber which is adapted to receive objects for cleaning and a spray system comprising nozzles for distributing liquid in the chamber, wherein the method comprising the steps of; introducing a first predetermined liquid volume to the chamber, circulating the first predetermined liquid volume by pumping liquid from the chamber to the spray system comprising nozzles for distributing the first predetermined liquid volume at the objects to be cleaned, subsequently opening a rapid transfer port which is liquid flow connected between the chamber and an outlet tank so as to constitute an immediate transfer of the first predetermined volume from the chamber to the outlet tank, essentially without any tubing arranged between the chamber and the outlet tank, closing the rapid transfer port for preparing the chamber to receive a second predetermined liquid volume to the chamber in a subsequent phase, and pumping the first predetermined liquid volume from the outlet tank to a sewer system for emptying the outlet tank.

Such a method provides a number of advantages, such as a reduced process time for a disinfection apparatus compared with prior-art technique. The combination of features achieve a quick fluid transfer time by an essentially direct transfer of liquid. By having the first predetermined liquid volume as a selected and preferably prepared volume makes it easier to have less complex components. This enhances the control of the parameters, such as the control of the liquid transfer, that has to be regulated. Additionally it is possible to reduce the costs and the number of machine components which may be costly, such as complex pumps and a plurality of valves. One pump may be used to circulate the fluid in the chamber without an intermediate tank wherein the liquid volume may be reduced which in turn may reduce the process time. Moreover the noise levels, relating to liquid transfer may be reduced.

By the expression "rapid transfer port" is meant a liquid port arranged to immediate transfer liquid from the chamber to the outlet tank.

By the expression "an immediate supply" is primary meant a substantially direct transfer of liquid and may be an instant and/or a spontaneous transfer. Thus, the liquid may be transferred from the chamber to the outlet tank, without any further flow control and/or without using any pumps.

Before introducing the first predetermined liquid volume to the chamber the method preferably comprises the step of introducing the first predetermined liquid volume to an inlet tank for preparing the first predetermined liquid volume. Such a preparation may further reduce the process time. The preparation may be one of a pre-measurement, premixing, dissolving of substances or similar preparations. Additionally the first predetermined liquid volume may substantially correspond to an adequate volume for a cleaning phase that is prepared. The cleaning phase may be one of the phases known for a washer disinfector such as one of; pre-wash, wash phase, rinse phase and/or disinfection phase. The disinfection phase may be achieved by a thermal disinfection and/or by an optional chemical phase with a chemical agent.

The first predetermined liquid volume is preferably released by opening an inlet port, the inlet port being of a rapid transfer port type, to immediately transferring the first liquid volume to the chamber for cleaning of objects. The time for the liquid transfer into the chamber may essentially be as quick as the time for the liquid transfer out of the chamber.

The introduction of the first predetermined liquid volume to the chamber may be performed without passing the nozzles, wherein less complex components may be used and the number of machine components may be reduced.

Additionally when circulating the first predetermined liquid volume, the liquid is being pressurized when being pumped from the chamber to the nozzles. The liquid is preferably pressurized all the way from the chamber pump to the nozzles wherein the liquid volume may be reduced. For instance, in such a case there is no need for an intermediate tank.

Moreover the immediate transfer between the chamber and the outlet tank is preferably achieved directly without any further flow control, wherein a safe and quick transfer may be achieved. Also, the cost and the number of machine components may be reduced.

The above objects are also achieved by a disinfection apparatus according to the introduction which is further characterised in that the chamber is adapted to receive a predetermined liquid volume which is being circulated by the spray system comprising nozzles for cleaning of objects, wherein the disinfection apparatus further comprises a rapid transfer port which is liquid flow connected between the chamber and an outlet tank so as to constitute an immediate transfer of the first predetermined volume from the chamber to the outlet tank, essentially without any tubing arranged between the chamber and the outlet tank.

The disinfection apparatus preferably having the corresponding advantages, aspects and features in relation to the above mentioned method.

By the expression "without any tubing" is primary meant a substantially direct transfer and may be achieved without any further flow control.

A passage for the immediate transfer of the first liquid volume from the chamber to the outlet tank may be adapted to constitute an unhindered passage for an essentially direct throughput without any further flow control. Such a passage reduces the liquid transfer time as the liquid is preferably unhindered externally the chamber.

By arranging an outlet of the chamber to constitute an inlet of the outlet tank an efficient fluid transfer is achieved. In use a liquid column may be at least indirectly defined in the chamber to perform a pressure on the transfer port thereby reducing efforts and costs in relation to prior-art technique.

The first predetermined volume to be directly transferred to the outlet tank may correspond to the required volume of a cleaning phase in the chamber. This enables a simplified efficient liquid transfer reducing the process time.

Additionally the first predetermined volume to be directly transferred to the outlet tank may be substantially the whole liquid volume in the chamber. Consequently this enhances and simplifies the regulation of the opening and closing of the transfer port. For instance a liquid level indicator may be arranged in the chamber for providing a signal to close the transfer port.

The chamber outlet is preferably arranged on a higher vertical level than an inlet of the outlet tank, wherein the transfer is achieved by means of gravity. Thus, the cost and the number of machine components may be reduced. The chamber outlet and the inlet of the outlet tank may at least partly separate the liquid by a sealing element in a closed position.

An inlet tank is preferably arranged which is adapted to introduce the first predetermined liquid volume to the chamber via an inlet port, the inlet port being of a rapid transfer port type. The inlet port having the corresponding advantages, aspects and features as mentioned for the rapid transfer port arranged between the chamber and the outlet tank.

The inlet port may be adapted to introduce the first predetermined liquid volume to the chamber without passing the nozzles.

A reduced process time may be achieved as the rapid transfer port preferably is adapted to transfer liquid at a flow velocity; preferably above 1 liters per second, more preferably above 2 liters per second and most preferably above 3 liters per second.

Moreover the first predetermined liquid volume to be transferred may be a volume between 10 and 150 liters, more preferably a volume between 15 to 70 liters and most preferably a volume between 20 to 55 liters. Thus the predetermined volume may be adapted to a so-called walk-in cabinet disinfector, but preferably not to a household dishwasher.

BRIEF DESCRIPTION OF THE DRAWINGS

The invention will in the following be described with reference to the accompanying drawings, which for the purpose of exemplification illustrate preferred embodiments of the invention.

FIG. 1 also shows a section along I-I of the disinfection apparatus.

DESCRIPTION OF PREFERRED EMBODIMENTS

Figure 1:
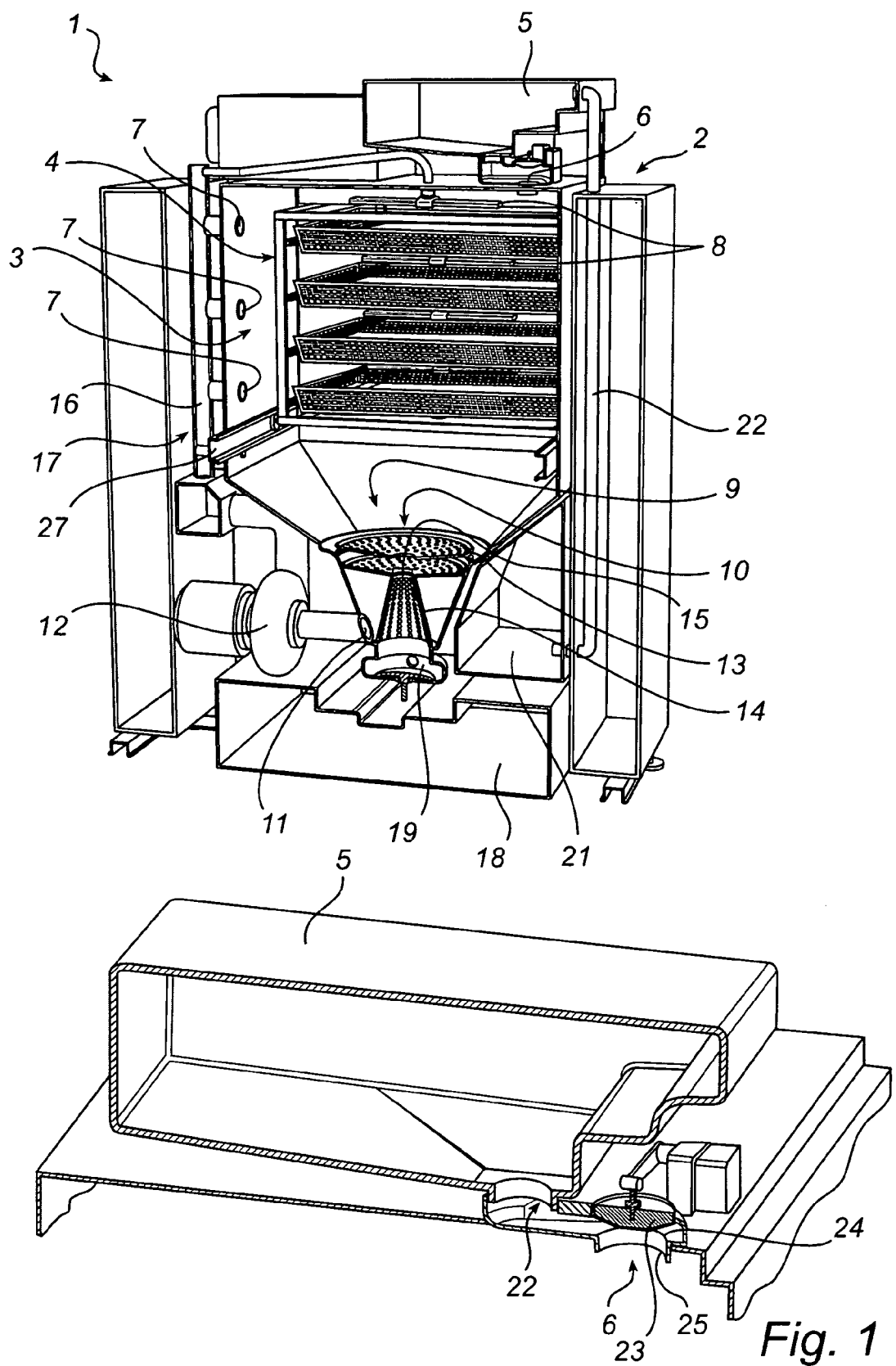
FIG. 1 is a schematic sectional view of a disinfection apparatus according to a first embodiment of the invention, seen obliquely from the rear.

FIG. 1 shows a disinfection apparatus 1 according to a first embodiment of the invention, which has a housing 2 in which a disinfection chamber 3 is arranged. The disinfection apparatus is adapted to perform at least a disinfection phase. The apparatus 1 is preferably an automatic and programmable washer disinfector which may be designed for central sterilization supply departments (CSSD), theatre sterile supply units (TSSU), and sub sterilization units, as well as for laboratories. The following are examples of objects to be washed, disinfected and dried in a disinfection program such as, surgical instruments, endoscopes, instruments for minimum invasive surgery, utensils, anesthetic and respiratory equipment, as well as bottles, glass jars and hollowware. The chamber 3 is adapted to receive objects to be disinfected which objects may be arranged on a wash cart 4 or on an insert. It is also possible to modify the wash carts 4 or inserts to actual load to almost any type of objects in any specific department.

The disinfector 1 has at least one door (not shown) for sealing the chamber 3 forming an enclosure. The door may be an automated door or for instance a manually operated vertically sliding down door. The apparatus 1 may alternatively be of a pass-through model arranged with two doors.

By providing an inlet tank 5, also called a stand-by tank, upstream the chamber to prepare the liquid to be used during the process in the chamber 3, the process time may be reduced. The chamber 3 is connected to several reservoirs (not shown) for instance for supplying at least one of deionised water, detergents, washing substances/liquids, rinse liquids, deliming agents, disinfection agents or other chemical agents. Such a supply may be achieved by a dosage pump. Thus depending on which program and which phase, for instance in a washing phase, additional agents is supplied to the chamber.

The inlet tank 5 is controllable connected to a water supply pipe (not shown).

An inlet port 6, preferably being a rapid transfer port type, is arranged in the lower part of the inlet tank 5. The inlet port 6 has a liquid passage which is adapted to transfer a significant volume per time unit, preferably above 2 liters per second.

FIG. 1 shows the wash cart 4 which is partly introduced in the chamber 3. The wash cart 4 in the form of a basket rack with multiple levels is guided by rails 27 in the chamber and which wash cart may be liquid/fluid connected in an active position. In this case the chamber exhibits three docking parts 7 for supplying liquid or fluid via corresponding docking parts at the wash cart 4. Spray arms 8, in the form of spray wings, are rotatably arranged in the chamber, in this case arranged at the upper and lower part of the chamber. Spray arms are also provided between the baskets at the wash cart 4. The spray arms have multiple arranged nozzles (not shown). It should be noted that wash carts or inserts may be of different designs and functions, such as provided with injector heads or ramps adapted for the objects to be received.

FIG. 1 further shows, a filter device 9 which is arranged at a collection space 10, or a sump, in the lower part of the chamber. The collection space 10 is connected to a pump inlet 11 of a circulation pump 12 for transferring the liquid being received in the chamber to the spray arms 8. The pump 12 pumps liquid from the lower part of the chamber. The filter device 9 has at least one essentially horizontal arranged filter plate 13, in this case two curved filter plates 13 with its concave side facing upwards. A peripheral filter element 14, which may be essentially cylindrical, or as in this case tapered, wherein the element 14 is essentially vertically arranged in the longitudinal direction. The components of the filter device 9 are preferably liquid permeable, and may be made of perforated metal plates or alternatively a filter mesh. The apertures of the filter device 9 is preferably smaller then the apertures of the spray arm nozzles/outlets. For instance the metal perforated plates may have perforations with a 3 mm times 3 mm spacing having an aperture diameter of 2 mm.

As seen in FIG. 1 the opening of the centre of the plates 13 defines a residue collection space 15 for washed off solids. The residue collection space 15 is preferably provided with a course filter (not shown). The course filter is preferably cup-shaped for collecting larger solid items and detachable for cleaning. The pump inlet 11 is arranged transversely and peripherally of the longitudinal direction of the collection space 10. The pump 12 is preferably a so-called low-pressure high-volume pump, in this case a centrifugal pump.

A circulation pipe 16 is arranged downstream the pump inlet 11 and the circulation pump 12 for circulating the liquid to the spray arms. The circulation pipe 16 is at least partly peripherally arranged with heating elements for heating the liquid which being circulated. The heating may for instance be achieved by steam, by electrical heating elements or by a combination thereof. The liquid flow from the inlet 11 of the circulation pump 12 to the spray arms 8 comprising nozzles defines a spray system 17 for subsequently distributing the liquid in the chamber after that the liquid has been descended into to the chamber 3 from the inlet tank 5. The liquid is preferably pressurized from the pump 12 to the spray arms 8 or to a corresponding device in the chamber 3.

A rapid transfer port 19, in the following called outlet port 19, is provided between the chamber 3 and an outlet tank 18, see FIG. 2. The outlet port 19 is adapted to transfer a significant volume per time unit, preferably above 2 liters per second. An essentially unhindered passage 30 is formed between the chamber 3 and the outlet tank 18, when the outlet port is changed from a closed position to an open position. The chamber outlet 32 is arranged to constitute an inlet 33 of the outlet tank 18 wherein the transfer is preferably achieved by means of gravity.

Figure 2:
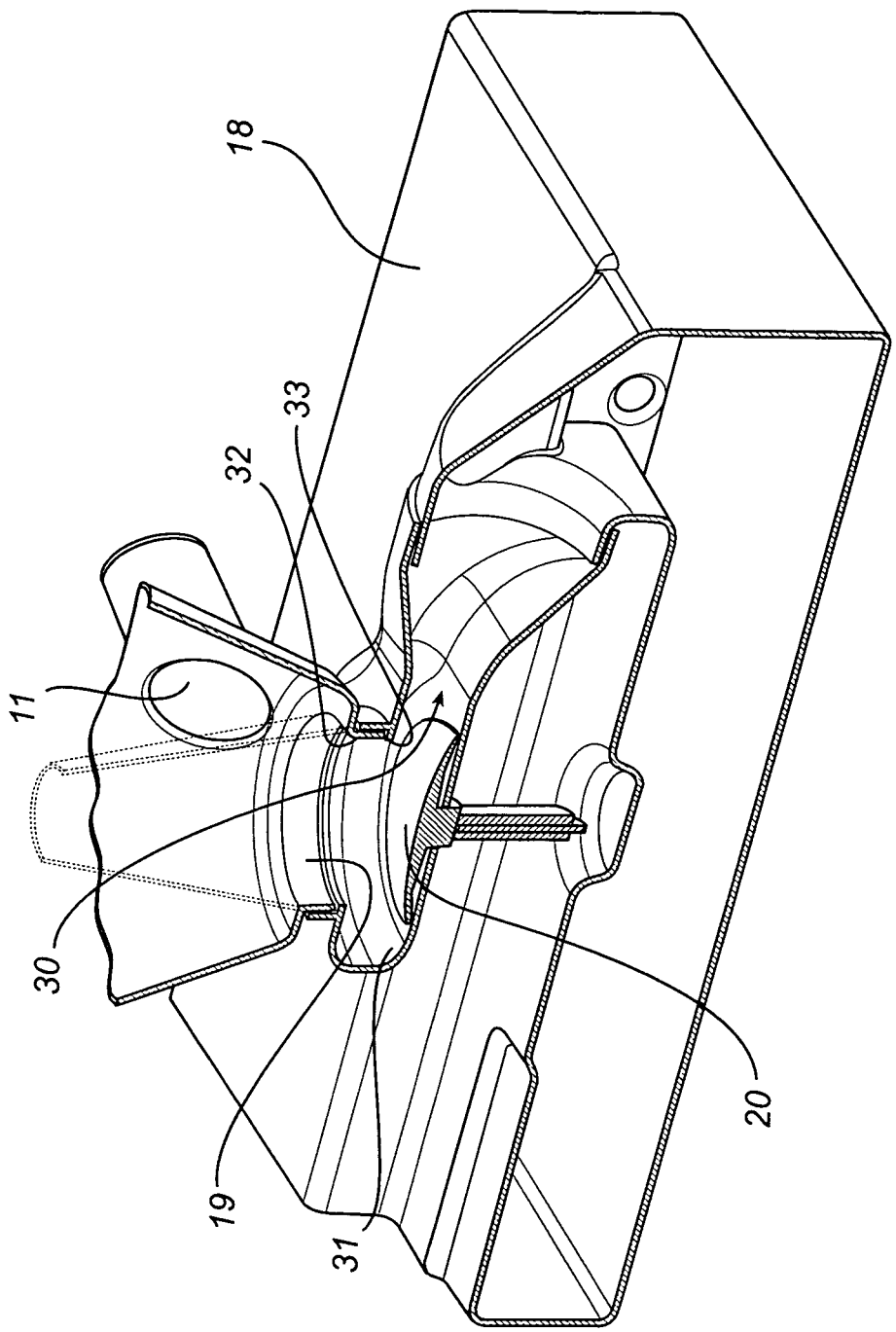
FIG. 2 shows in more detail parts of the disinfection apparatus in FIG. 1, partly in section.

FIG. 2 shows that the outlet port 19 is in liquid communication with the outlet tank 18. An outlet sealing element 20 is controllably arranged at the outlet port 19 for sealing of the passage 30. The outlet sealing element 20 may be a plate valve which is slidingly arranged between an opened and a closed position. Preferably the outlet sealing element 20 in the opened position, has at least a partly peripheral space 31 at the outlet tank defining the passage 30. Downstream the peripheral space 31, the outlet tank is at least partly frustum conical or baffle-shaped to efficiently receive the liquid from the chamber.

In order to save space, the outlet tank 18 may extend more in the horizontal direction than in the vertical direction.

By providing a separate preparation tank 21 connected to the inlet tank liquids may be prepared during previous program phases in order to save process time. The separate preparation tank 21 is controllable connected to a water supply conduit (not shown). In this embodiment preparation elements, preferably heating means, such as heating elements (not shown) are arranged in the preparation tank to prepare the liquid used for the disinfection phase of the disinfection program. As exemplified above other kind of preparations are possible. The liquid, in this case essentially water, is preferably heated to a temperature between 75 to 99° C., more preferably to a temperature between 82 to 97° C. and most preferably to a temperature between 85 to 95° C. As the preparation tank 21 is arranged upstream the inlet tank 5, the inlet tank may be disinfected before the liquid is transferred to the chamber 3. In this case the separate preparation tank 21 is arranged at the lower part of the disinfection apparatus. However the separate preparation tank 21 may be arranged at other places, for instance above the chamber and alternatively additionally above the inlet tank 5. If a chemical disinfection is performed the temperature may be lower, e.g. approximately 60° C.

FIG. 1 with the enlarged inlet tank 5 shows that the interior of the inlet tank 5 has sloping surfaces to a communication section 22. An inlet sealing element 23 is moveably arranged at the inlet port 6 between an opened and a closed position. The sealing element 23 may be arranged with an arm which is pivotable for regulating the liquid transfer through the inlet port 6. However other kind of sealing elements are possible such as one of a sliding sealing element, a tilting element, a butterfly valve or a piston valve. Preferably, an outlet 24 of the inlet tank 5 constitutes the inlet 25 of the chamber 3, which are separated by the inlet sealing element 23 in the closed position. Thus, as seen in FIG. 1, the transfer is preferably achieved by means of gravity.

A disinfection program may comprise of different components but usually comprises, at least one of; pre-washing, washing, rinsing and/or disinfection. It should be noted that numerous different programs and parameters may be selected by a person skilled in the art.

FIG. 3a to FIG. 3d shows a sequence of liquid transfer in a general way at the disinfection apparatus as described above. As mentioned above the separate preparation tank 21 is advantageously supplied with, liquid, preferably water, in an early stage for heating the liquid to be used in the disinfection phase.

Figure 3A:
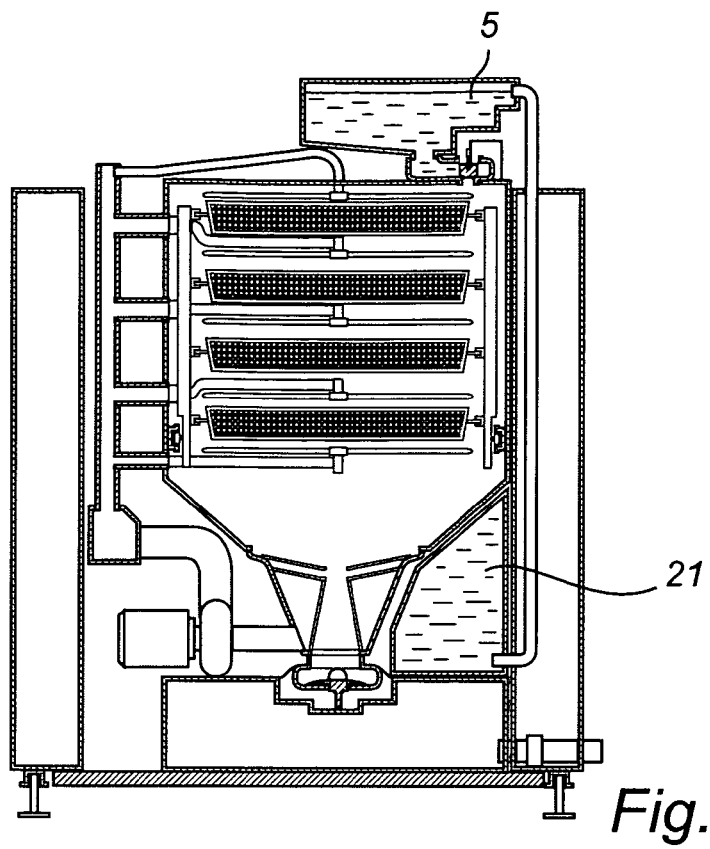
FIG. 3a-3d shows a sequence of liquid transfer of the disinfection apparatus in FIG. 1.

As seen in FIG. 3a, the inlet tank 5 is supplied with essentially a predetermined volume, preferably water. The predetermined liquid volume is preferably measured during the supply by a liquid indicator (not shown) arranged in the inlet tank 5.

Figure 3B:
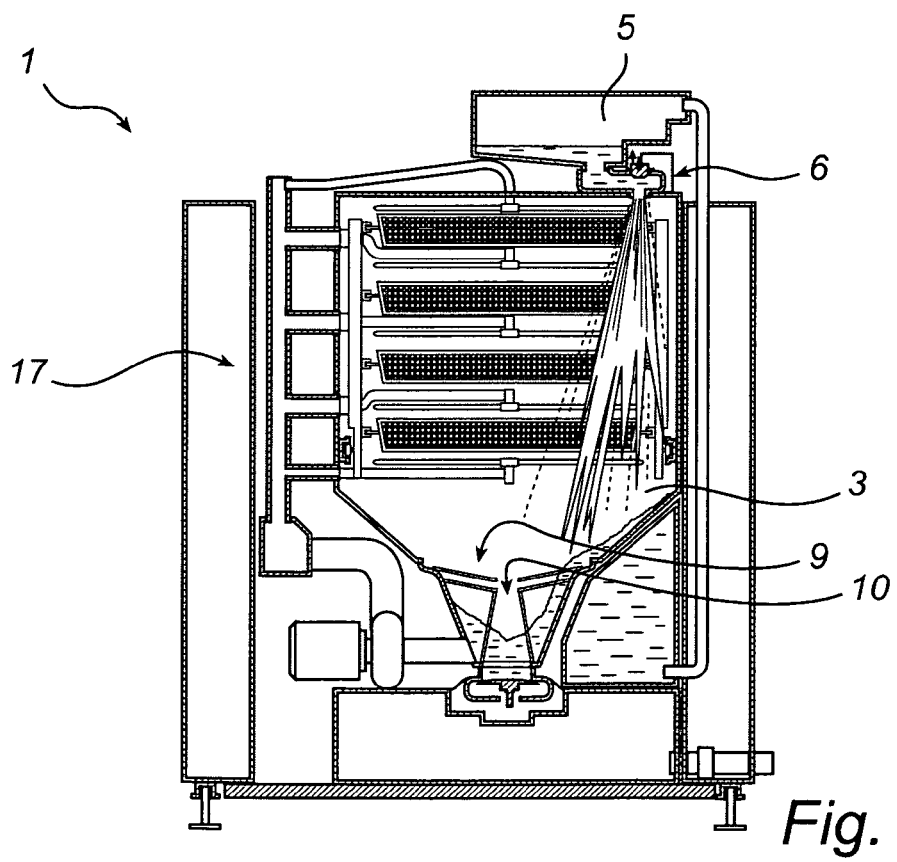

FIG. 3b shows the phases of opening an inlet port 6 for transferring the (first) predetermined liquid volume to the chamber 3. The liquid indicator senses when the inlet port 6 may close. For instance if additional water should be needed for a specific phase, the inlet port 6 and the water supply pipe may remain opened for a selected time. As mentioned above additional cleaning agents may be separately supplied to the chamber depending on the program and the program phase, such as a washing phase. After closing the port 6, to a preferably empty inlet tank 5, a second predetermined liquid volume may be introduced to the inlet tank 5. However it should be noted that the above introducing phase may be performed during other phases, for instance simultaneously during one of the FIG. 3c phases.

Figure 3C:
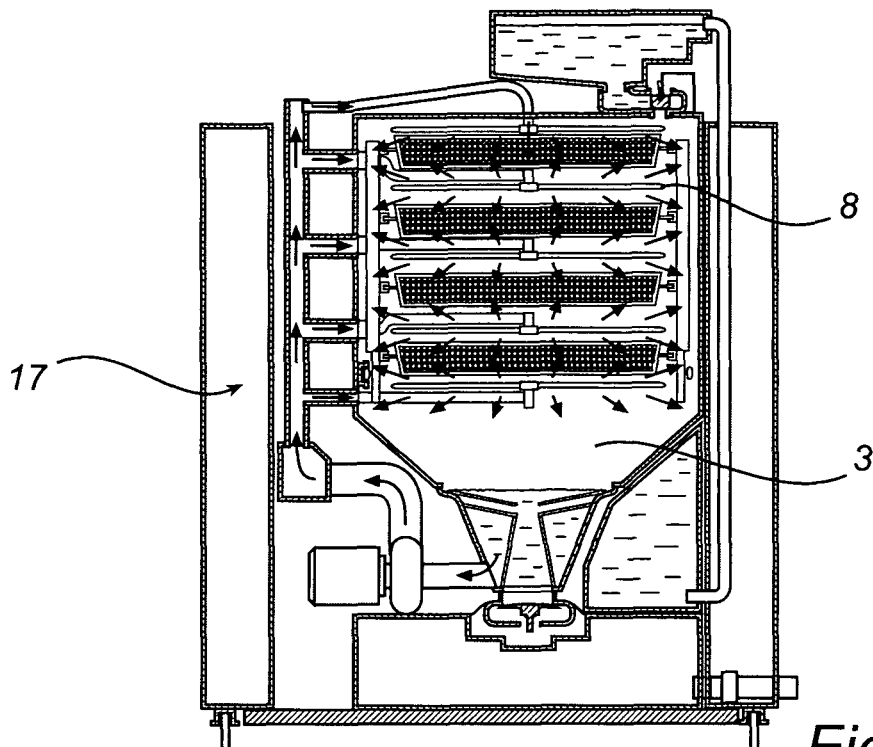

Referring to FIG. 3c which shows a part of the sequence which preferably is repeated during a selected time which depends on the selected program and the selected parameters. The descended liquid in the chamber is pumped from the chamber 3 to the spray system 17 with spray arms 8. When the liquid being draw into the pump inlet 11, it is filtered by the filter device 9 arranged at the collection space 10 in the chamber.

The liquid may be heated at least along a part of the path between the chamber 3 and the spray arm 8. In this case the liquid is heated at the circulation pipe 16 by heating elements. The liquid is subsequently distributed and spread by the spray arms 8 or by similar nozzle device within the chamber 3.

Figure 3D:
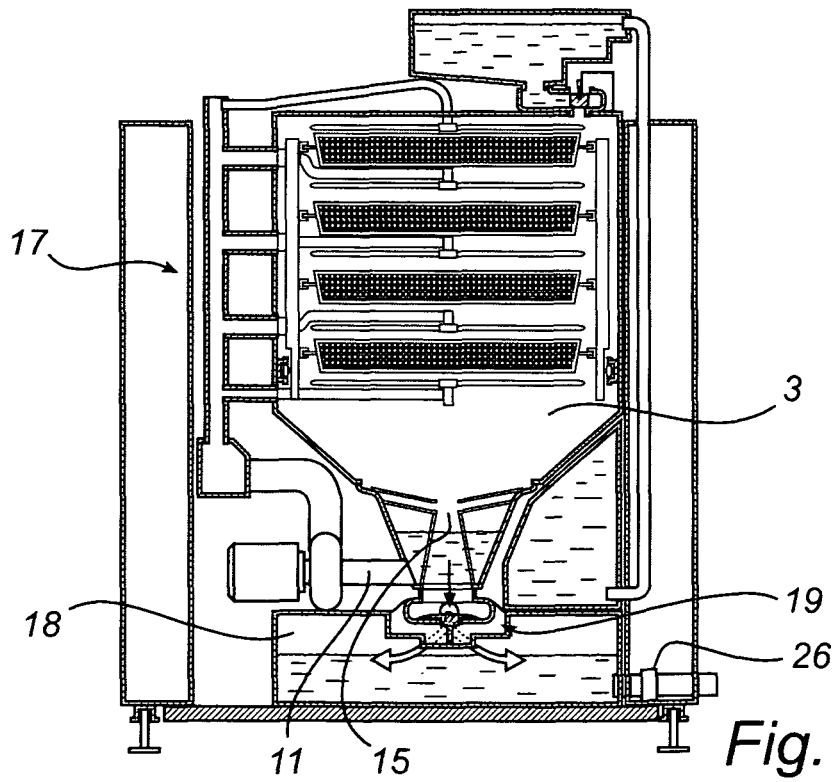

When the predetermined liquid volume being circulated a selected time, the shown phase in FIG. 3d is performed;

opening an outlet port 19 for transferring the predetermined liquid volume to the outlet tank 18. The filter device is preferably cleaned to some extent by the flow of the liquid transfer from the chamber 3 to the outlet tank 19. As mentioned above larger items are received in the residue collection space 15 by the course filter. Afterwards the outlet port 19 is closed after a preset time or an indicted absence of liquid in the chamber 3.

Figure 4:
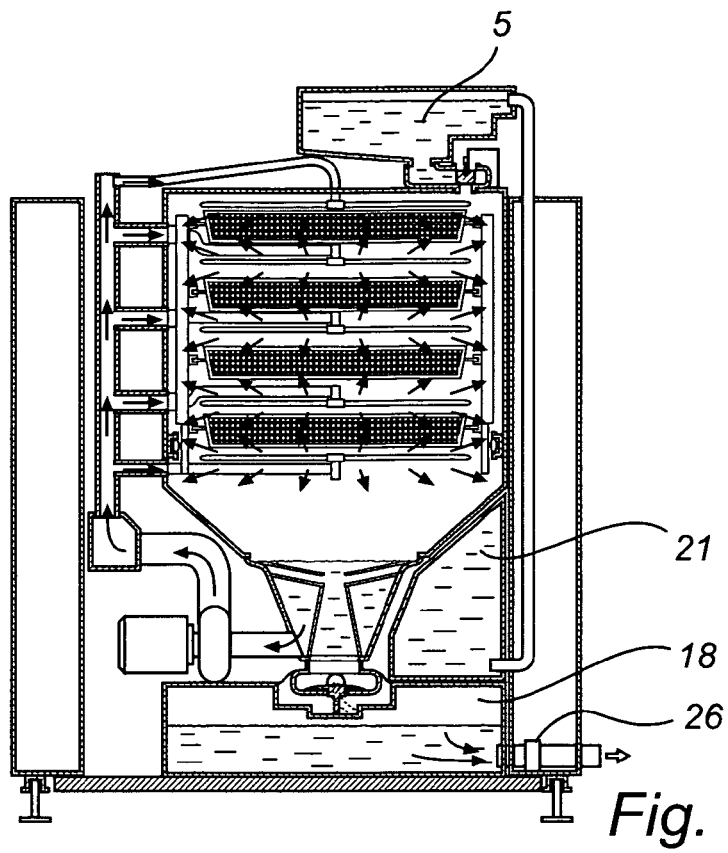
FIG. 4 shows the disinfection apparatus in FIG. 1 in an emptying phase.

FIG. 4 shows an exhaust pump 26 connected to a sewer system (not shown) to exhaust the liquid from the outlet tank 18. Such operation may be performed during a suitable time gap, preferably when no additional liquid is supplied to the outlet tank, for instance during one of the following phases; when liquid is supplied to the chamber or the inlet tank, when liquid is circulated by the circulation pump 12 or after the final phase in a selected program.

Figure 5A:
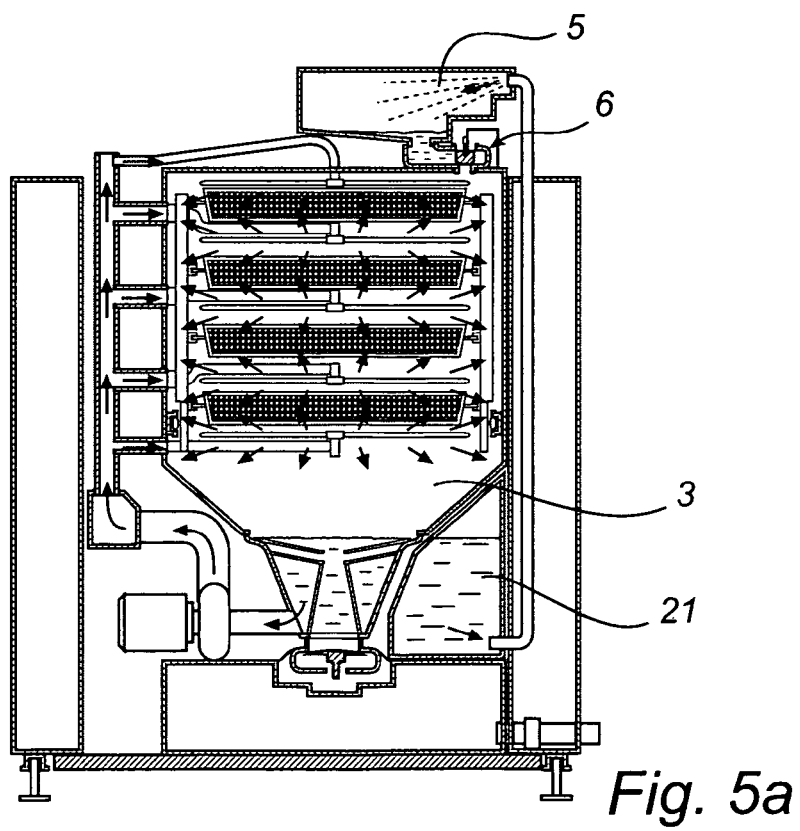
FIG. 5a-5b shows a part of a sequence in a disinfection phase, of the disinfection apparatus in FIG. 1.
Figure 5B:
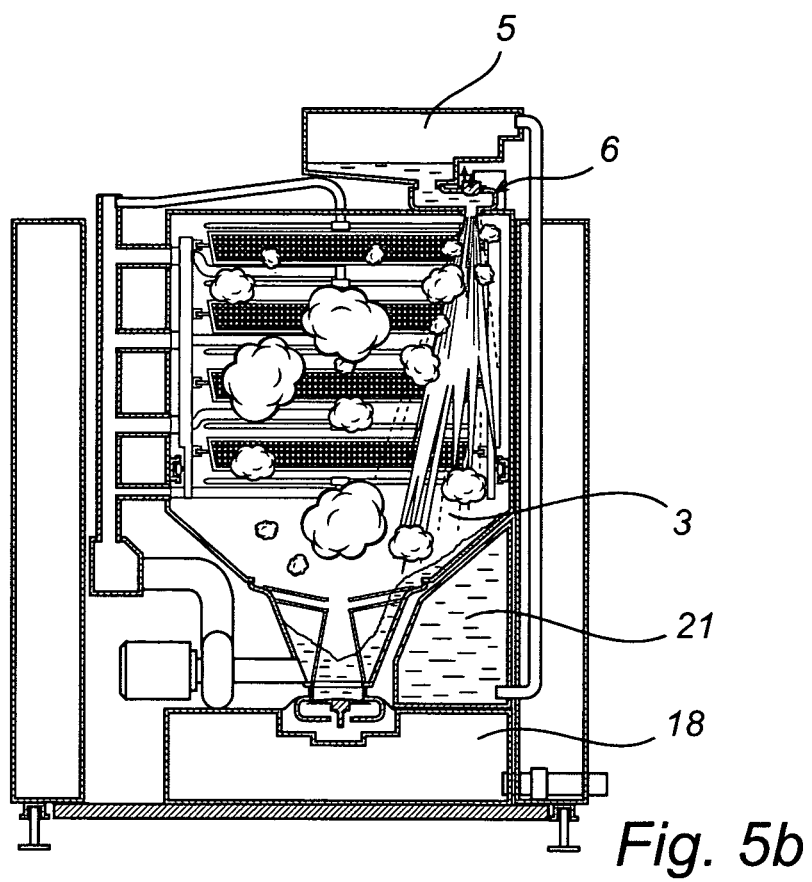

FIG. 5a-5b shows an example of how a separate preparation tank 21 may be used according to the invention. As the heating of water for a disinfection phase is time consuming, the separate preparation tank is preferably supplied with water in an early stage of the program or alternatively already in the previous program.

The transfer of liquid from the preparation tank 21 to the inlet tank 5 is preferably performed during an active phase of a program, such as when liquid being circulated in the chamber as in FIG. 5a. Alternatively, the sequence shown in 5a-5b may be performed during an inactive phase.

The liquid transfer of the disinfection apparatus is carried out by transferring a predetermined liquid volume, from the preparation tank 21 to the inlet tank 5. In this case the transfer is achieved by pumping the liquid.

Subsequently, the inlet tank may be disinfected during a preset time. Afterwards the inlet port 6 is opened for transferring the predetermined liquid volume to the chamber 3 (see FIG. 5b). Subsequently the interior of the chamber 3 and the present objects are disinfected, preferably by hot liquid disinfection as described above.

The liquid transfer in the disinfection phase may be performed essentially in the same way as described above, according to the sequence in FIG. 3c showing when the liquid is being circulated and in FIG. 3d showing the transfer to outlet tank 18. Depending on the selected program or the selected subsequent program or phase, the inlet tank 5 and/or the separate preparation tank 21 may be empty or alternatively at least partly refilled. For instance a predetermined liquid volume may be introduced into the preparation tank 21 to prepare for the next program as shown in FIG. 5b.

Partly referring to FIG. 4, the liquid transferred to the outlet tank 18 is preferably pumped to the sewer by the sewer pump 26 when the liquid is below a predetermined liquid temperature. Alternatively the temperature may be adjusted by mixing of colder liquids.

Also, the pH-value of the liquid in the outlet tank may be adjusted by pH-regulating liquid/substance, if the pH-value is diverging from an accepted level after one of the cleaning phases, for instance after a so-called chemical phase.

It will be appreciated that the above-described embodiment of the invention can be modified and varied by a person skilled in the art without departing from the inventive concept defined in the claims. For instance the disinfection apparatus may be provided with more than one outlet tank and/or inlet tank in order to perform different treatments of the liquid. Additionally the disinfection apparatus may comprise several rapid transfer ports. The inlet and/or the outlet tank is preferably adapted to receive liquid from at least on cleaning phase of a program, For instance, the tank may be adapted to receive the liquid for more than one phase, such as two phases.

The invention claimed is:

1. A liquid disinfection apparatus for cleaning of objects, comprising:
    a chamber, arranged to receive said objects for cleaning;
    at least one door configured to seal said chamber;
    an inlet tank positioned above the chamber;
    a controllable inlet port fluidly connecting the inlet tank to the chamber to introduce a liquid volume into the chamber;
    a spray system including nozzles for distributing the liquid volume in said chamber for cleaning of the objects;
    an outlet tank fluidly coupled to the chamber, the outlet tank being connected to a sewer system;
    a controllable outlet port fluidly connecting the chamber and the outlet tank, the controllable outlet port being configured to transfer liquid at a flow velocity above 1 liter per second; and
    an outlet sealing element controllably arranged at the controllable outlet port for sealing the controllable outlet port,
    wherein the outlet tank, downstream of a passage formed between the chamber and the outlet tank when the sealing element is in its open position, is at least partly frustum conical in shape to efficiently receive the liquid volume from the chamber.

2. The disinfection apparatus as claimed in claim 1, wherein the passage for the transfer of said liquid volume from said chamber to said outlet tank is adapted to constitute an unhindered passage for an essentially direct throughput without any further flow control.

3. The disinfection apparatus as claimed in claim 1, wherein an outlet of said chamber is arranged to constitute an inlet of said outlet tank.

4. The disinfection apparatus as claimed in claim 1, wherein said liquid volume to be directly transferred to said outlet tank corresponds to the required volume of a cleaning phase in said chamber.

5. The disinfection apparatus as claimed in claim 1, wherein said liquid volume to be directly transferred to said outlet tank is substantially the whole liquid volume in said chamber.

6. The disinfection apparatus as claimed in claim 1, wherein the chamber outlet is arranged on a higher vertical level than an inlet of the outlet tank, wherein the transfer is achieved via gravity.

7. The disinfection apparatus as claimed in claim 1, wherein said inlet port is adapted to introduce said liquid volume to said chamber without passing said nozzles.

8. The disinfection apparatus as claimed in claim 1, wherein said outlet tank has a volume of at least between 10 and 150 liters, the chamber being adapted to receive between 10 and 150 liters of liquid.

9. The disinfection apparatus as claimed in claim 1, wherein said controllable outlet port is configured to transfer liquid at a flow velocity above 2 liters per second.

10. The disinfection apparatus as claimed in claim 1, wherein said liquid volume to be transferred is a volume between 15 to 70 liters.

11. The disinfection apparatus as claimed in claim 1, wherein said controllable outlet port is configured to transfer liquid at a flow velocity above 3 liters per second.

12. The disinfection apparatus as claimed in claim 1, wherein said liquid volume to be transferred is a volume between 20 to 55 liters.

13. The disinfection apparatus of claim 1, wherein the controllable outlet port directly connects the chamber to the outlet tank without any tubing between the chamber and the outlet tank.

14. The disinfection apparatus of claim 1, wherein,
the liquid volume corresponds to a volume of liquid for a complete cleaning phase, the complete cleaning phase being one of a pre-wash phase, a wash phase, a rinse phase and a disinfection phase,
the inlet tank and the outlet tank each being sized to hold the liquid volume.

15. The disinfection apparatus of claim 1, further comprising:
a sewer pump fluidly connected to the outlet tank, the sewer pump being configured to discharge liquid from the outlet tank once a temperature of the liquid in the outlet tank is below a predetermined liquid temperature.

16. The disinfection apparatus of claim 1, wherein the outlet tank is located below the chamber.

17. A liquid disinfection apparatus for cleaning of objects, comprising:
a chamber, arranged to receive said objects for cleaning;
at least one door configured to seal said chamber;
a spray system including nozzles for distributing a liquid volume in said chamber for cleaning of the objects;
an outlet tank positioned below the chamber;
a controllable outlet port directly connecting the chamber and the outlet pert tank without any tubing between the chamber and the outlet tank, the controllable outlet port being configured to transfer liquid at a flow velocity above 1 liter per second; and
an outlet sealing element controllably arranged at the controllable outlet port for sealing the controllable outlet port,
wherein the outlet tank, downstream of a passage formed between the chamber and the outlet tank when the sealing element is in its open position, is at least partly frustum conical in shape to efficiently receive the liquid volume from the chamber.

18. The disinfection apparatus of claim 17, further comprising:
an inlet tank positioned above the chamber;
a controllable inlet port fluidly connecting the inlet tank to the chamber to introduce the liquid volume into the chamber.

* * * * *